US00PP24146P2

(12) United States Plant Patent
Bergman

(10) Patent No.: US PP24,146 P2
(45) Date of Patent: Jan. 7, 2014

(54) ***CHRYSANTHEMUM* PLANT NAMED 'CIDZ0034'**

(50) Latin Name: *Chrysanthemum×morifolium*
Varietal Denomination: CIDZ0034

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 76 days.

(21) Appl. No.: 13/506,914

(22) Filed: May 24, 2012

(51) Int. Cl.
*A01H 5/00* (2006.01)

(52) U.S. Cl.
USPC ..... Plt./298

(58) Field of Classification Search
USPC ..... Plt./298
See application file for complete search history.

(56) References Cited

PUBLICATIONS

UPOV PLUTO 201303 BR Citation for CIDZ0034 Aug. 14, 2012.*
UPOV PLUTO 201303 CA Citation for CIDZ0034 Oct. 31, 2011.*

* cited by examiner

*Primary Examiner* — Wendy C Haas
(74) *Attorney, Agent, or Firm* — Joshua L. Price

(57) ABSTRACT

A new *Chrysanthemum* plant named 'CIDZ0034' particularly distinguished by the red colored anemone-type inflorescences that have good color retention, has a very uniform growth habit and a 7.5 week flowering response.

1 Drawing Sheet

Latin name of the genus and species of the plant claimed: *Chrysanthemum×morifolium.*

Varietal denomination: 'CIDZ0034'.

BACKGROUND OF THE NEW PLANT

The present invention comprises a new *Chrysanthemum*, botanically known as *Chrysanthemum×morifolium*, and hereinafter referred to by the variety name 'CIDZ0034'.

'CIDZ0034' is a product of a planned breeding program. The new cultivar has red colored anemone-type inflorescences that have good color retention, has a very uniform growth habit and a 7.5 week flowering response.

'CIDZ0034' originated from a hybridization made in March 2008 in a greenhouse in Bogota, Colombia. The female parent was the unpatented, proprietary plant designated 'YB-B2899'. 'YB-B2899' has purple colored, single-type inflorescence and a faster flowering response time than that of 'CIDZ0034'.

The male parent of 'CIDZ0034' was an unpatented, proprietary plant identified as 'YB-B2956'. 'YB-B2956' has red colored anemone-type inflorescence, a little more color fading habit and a more upright growth habit than that of 'CIDZ0034'. The resultant seed was sown in October 2008 in a shade structure in Fort Myers, Fla.

'CIDZ0034' was selected as one flowering plant within the progeny of the stated cross in March 2009, grown in pots in a shade structure in Fort Myers, Fla.

The first act of asexual reproduction of 'CIDZ0034' was accomplished when vegetative cuttings were propagated from the initial selection in June 2009 in a greenhouse in Fort Myers, Fla.

BRIEF SUMMARY OF INVENTION

Horticultural examination of plants grown from cuttings of the plant initiated in March 2009, and continuing thereafter, has demonstrated that the combination of characteristics as herein disclosed for 'CIDZ0034' are firmly fixed and are retained through successive generations of asexual reproduction.

'CIDZ0034' has not been observed under all possible environmental conditions. The phenotype may vary significantly with variations in environment such as temperature, light intensity, and day length.

Plant Breeder's Right for this cultivar were applied for in Canada on Jul. 29, 2011, No. 11-7350 and in Brazil on 14 Aug. 2012, Application number 218060001832012. 'CIDZ0034' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0034' with colors being as true as possible with an illustration of this type.

Figure 1:
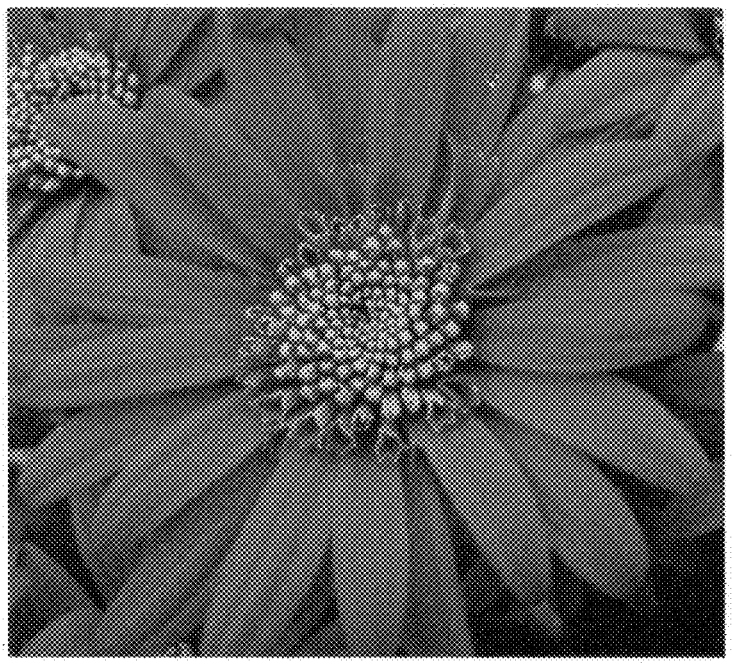
Figure 2:
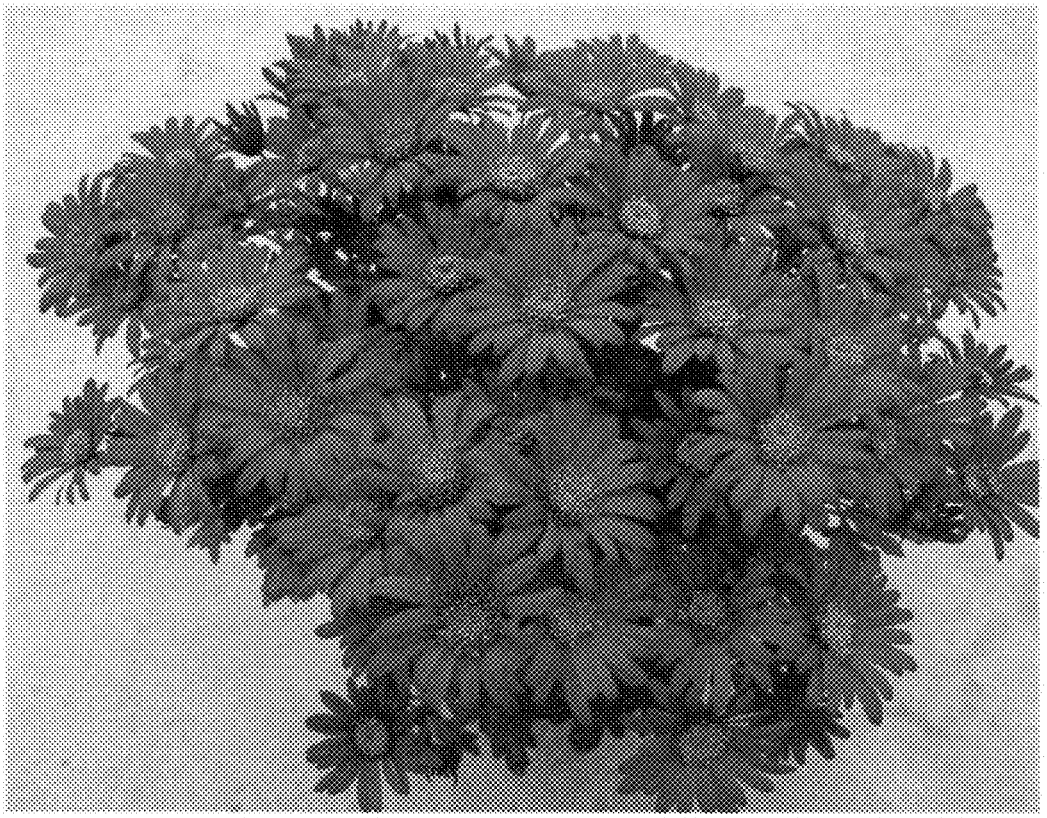

The photographic drawings show in FIG. 1, a close-up of the inflorescence and in FIG. 2, 4 flowering plants of the new variety.

DETAILED BOTANICAL DESCRIPTION

The plant descriptions, measurements and aforementioned photographs were taken in Gilroy, Calif. in January 2012 under natural light. These plants were grown 4 plants in a 5-inch pot under center bud removal and blackcloth controlled greenhouse trial conditions in Gilroy, Calif. These plants were 10-12 weeks old.

Color references are made to The Royal Horticultural Society Colour Chart (R.H.S.) 2001.

TABLE 1

DIFFERENCES BETWEEN THE NEW VARIETY 'CIDZ0034' AND TWO MOST SIMILAR VARIETIES

| | 'CIDZ0034' | 'Red Yoirvine' (U.S. Plant Pat. No. 19,174) (compared for color and like petal type) |
|---|---|---|
| Ray floret color: | Red | Deeper, little more purple red |
| Ray floret form: | Ligulate | Ligulate |
| Inflorescence form: | Anemone | Single-daisy |
| Inflorescence size: | Smaller | Larger |
| Blackcloth flowering response: | Faster | Slower |

| | 'CIDZ0034' | 'Yoencino' (U.S. Plant Pat. No. 21,563) (compared for inflorescence form) |
|---|---|---|
| Inflorescence form: | Anemone | Anemone |
| Ray floret form: | Ligulate | Spoon |
| Ray floret color: | Red | More greyed-red |
| Flowering response time: | 1 week faster | 1 week slower |

Plant:

*Form, growth and habit*.—Herbaceous pot-type, stems upright and outwardly spreading, freely branching, strong and moderately vigorous growth habit.

*Plant height*.—20.0-22.0 cm.

*Plant height* (*inflorescence included*).—25.0-28.0 cm.

*Plant width*.—20.0-25.0 cm.

Roots:

*Number of days to initiate roots*.—4-5 days at about 22 degrees C.

*Number of days to produce a rooted cutting*.—10-12 days at 22 degrees C.

*Type*.—Fine, fibrous, free branching.

*Color*.—RHS N155B but whiter.

Foliage:

*Arrangement*.—Alternate.

*Immature, leaf color, upper surface*.—Closest to RHS 147A.

*Lower surface*.—Closest to RHS 147B.

*Mature, leaf color, upper surface*.—RHS 147A mottled with RHS 147B.

*Lower surface*.—Closest to RHS 147B.

*Length*.—6.5-7.0 cm.

*Width*.—4.0-5.7 cm.

*Shape*.—Ovate.

*Base shape*.—Attenuate.

*Apex shape*.—Mucronulate.

*Margin*.—Palmately lobed; irregularly incised, and slightly serrate.

*Texture, upper surface*.—Bifid T-shaped hairs.

*Lower surface*.—Bifid T-shaped hairs.

*Color of veins, upper surface*.—RHS 138B.

*Color of veins, lower surface*.—RHS 138B.

*Pattern of veining*.—Palmate.

*Petiole color*.—RHS 138B.

*Length*.—2.3-2.5 cm.

*Diameter*.—0.3 cm.

*Texture*.—Bifid T-shaped hairs.

Stem:

*Quantity of main branches per plant*.—4-6.

*Color of stem*.—RHS 137C but appears lighter due to hair.

*Length of stem*.—18.0-20.0 cm.

*Diameter*.—0.35-0.4 cm.

*Length of internodes*.—0.7-2.0 cm.

*Texture*.—Bifid T-shaped hairs.

*Color of peduncle*.—RHS 137C.

*Length of peduncle*.—6.5-7.3 cm.

*Peduncle diameter*.—0.2 cm.

*Texture*.—Bifid T-shaped hairs.

Inflorescence:

*Type*.—Compositae type, solitary single-type inflorescences, borne terminally above foliage, ray florets arranged acropetally on a capitulum.

*Quantity of short days to flowering* (*response time*).—7.5 weeks.

*Natural season flowering*.—Not determined on this variety.

*Quantity of inflorescences per plant*.—19-21 plus 1-4 buds.

*Lastingness of individual blooms on the plant*.—4 weeks.

*Fragrance*.—Slightly spicy.

Bud (just when opening/showing color):

*Color*.—RHS 187B but slightly lighter.

*Length*.—1.4-1.7 cm.

*Width*.—1.0-1.3 cm.

*Shape*.—Elongated oblate.

Immature inflorescence:

*Diameter*.—6.3-6.5 cm.

*Color of ray florets, upper surface*.—Between RHS 53A and RHS 187C.

*Lower surface*.—RHS 184A.

Mature inflorescence:

*Diameter*.—7.0-7.5 cm.

*Depth*.—2.0 cm.

*Total diameter of disc*.—2.5-3.0 cm.

*Receptacle color*.—RHS 144B.

*Receptacle height*.—0.3 cm.

*Receptacle diameter*.—0.4 cm.

Ray florets:

*Average quantity of florets*.—23-24 in 2 whorls.

*Color of florets, upper surface*.—Closest to and between than RHS 46A and RHS 46B that appears in a slight cross-hatched pattern with RHS 3C basally.

*Lower surface*.—RHS 185A and a slightly deeper hue, that appears in a slight cross-hatched pattern over RHS 180C with RHS 3C basally.

*Length*.—3.7-4.0 cm.

*Width*.—0.75-0.8 cm.

*Shape*.—Elliptical.

*Apex shape*.—Obtuse.

*Margin*.—Entire.

*Texture, upper surface*.—Papillose.

*Lower surface*.—Papillose.

Disc florets:

*Average quantity of florets*.—About 140.

*Color of florets, inside*.—Darker than RHS 46A with RHS 6b apex.

*Outside*.—Mostly RHS 46B somewhat overlaid with RHS 6B and RHS 6B apex.

*Length*.—0.8-1.5 cm.

*Width*.—0.1-0.2 cm.

*Shape*.—Tubular, elongated.

*Apex shape*.—Acute, 5 pointed.

Phyllaries:

*Quantity*.—20-25.

*Color, upper surface*.—RHS 137C.

*Lower surface*.—RHS 137A.

*Length.*—0.4-0.5 cm.
*Width.*—0.2 cm.
*Shape.*—Lanceolate.
*Apex shape.*—Acute.
*Base.*—Fused.
*Margins.*—Entire; slightly papery.
*Texture, upper surface.*—Glabrous.
*Lower surface.*—Bifid T-shaped hairs.

Reproductive organs:

*Pistil.*—1, found on both types of florets.
*Length.*—0.6 cm.
*Style color.*—RHS 1C.
*Style length.*—0.5 cm.
*Stigma color.*—RHS 1B.
*Stigma shape.*—Bi-parted.
*Ovary color.*—RHS 155C.
*Ovary length.*—0.05 cm.
*Ovary width.*—0.05 cm.
*Stamens.*—4, found on only on the disc florets.
*Color of filaments.*—RHS 155C.
*Length filaments.*—0.3-0.4 cm.
*Anther color.*—RHS 15A.
*Anther length.*—0.1 cm.
*Anther shape.*—Oval.
*Color of pollen.*—Between RHS 17B to RHS 17C.
*Pollen amount.*—Abundant.
*Fertility/seed set.*—Has not been observed to date.
*Disease/pest resistance.*—Has not been observed to date.

What is claimed is:

1. A new and distinct variety of *Chrysanthemum* plant named 'CIDZ0034' substantially as illustrated and described herein.

* * * * *